(12) United States Patent
Wang et al.

(10) Patent No.: US 10,265,358 B2
(45) Date of Patent: Apr. 23, 2019

(54) METHOD FOR THE PREPARATION OF MEDICATED LEAVEN MASSA BY PURE STRAIN FERMENTATION

(71) Applicants: Qiuhong Wang, Panyu District, Guangzhou, Guangdong (CN); Guangdong Pharmaceutical University, Guangzhou, Guangdong (CN); Haixue Kuang, Harbin, Heilongjiang Province (CN)

(72) Inventors: Qiuhong Wang, Guangzhou (CN); Haixue Kuang, Harbin (CN); Zunpeng Shu, Guangzhou (CN); Changfu Wang, Guangzhou (CN)

(73) Assignees: Qiuhong Wang, Guangzhou, Guangdong (CN); Guangdong Pharmaceutical University, Guangzhou, Guangdong (CN); Haixue Kuang, Harbin, Heilongjiang Province (CN)

( * ) Notice: Subject to any disclaimer, the term of this patent is extended or adjusted under 35 U.S.C. 154(b) by 119 days.

(21) Appl. No.: 15/185,312

(22) Filed: Jun. 17, 2016

(65) Prior Publication Data
US 2016/0367610 A1    Dec. 22, 2016

(30) Foreign Application Priority Data
Jun. 19, 2015  (CN) .......................... 2015 1 0340237

(51) Int. Cl.
| | | |
|---|---|---|
| *A61K 36/28* | (2006.01) | |
| *A61K 36/48* | (2006.01) | |
| *A61K 36/62* | (2006.01) | |
| *A61K 36/73* | (2006.01) | |
| *A61K 36/282* | (2006.01) | |
| *A61K 36/704* | (2006.01) | |
| *C12N 1/14* | (2006.01) | |
| *A61K 36/062* | (2006.01) | |
| *C12P 1/02* | (2006.01) | |

(52) U.S. Cl.
CPC ............ *A61K 36/062* (2013.01); *A61K 36/28* (2013.01); *A61K 36/282* (2013.01); *A61K 36/48* (2013.01); *A61K 36/704* (2013.01); *A61K 36/73* (2013.01); *C12N 1/14* (2013.01); *C12P 1/02* (2013.01); *A61K 2236/19* (2013.01)

(58) Field of Classification Search
None
See application file for complete search history.

(56) References Cited

U.S. PATENT DOCUMENTS

| | | |
|---|---|---|
| 2,438,911 A | 4/1948 | Gronningsaeter |
| 3,506,435 A | 4/1970 | Themelis |
| 2015/0322546 A1 | 11/2015 | Zhou |

FOREIGN PATENT DOCUMENTS

| | | |
|---|---|---|
| CN | 101705360 A | 5/2010 |
| CN | 101736112 A | 6/2010 |
| JP | S48-029961 B1 | 9/1973 |
| JP | 2016-501315 | 1/2016 |

OTHER PUBLICATIONS

First Office Action in Japanese Application No. 2015-545661 dated May 24, 2016; 6 pages including English summary.
Shandong food and Drug Administration (2012), Specifications for processing Chinese Herbal Pieces in Shandong, p. 116 "Massa Medicata Fermentata". Shandong Science and Technology Press, Shandong province, China. Including English translation of preparation method part.
Ren QL, Song XX (2010). "Analysis of the quality of Medicated Leaven Massa" Chinese Journal of Modern Drug Application 4(10): 113-114. Including English translation of preparation method part.

*Primary Examiner* — Soren Harward
*Assistant Examiner* — Paul D. Pyla
(74) *Attorney, Agent, or Firm* — Schwabe Williamson & Wyatt, PC

(57) ABSTRACT

The present invention relates to a method for the preparation of Medicated Leaven Massa by pure strain fermentation, characterized in that the Medicated Leaven Massa is prepared by fermentation under suitable conditions with *Penicillium chrysogenum* as a single fermentative strain and the culture medium is made of 6 ingredients, including flour (and/or wheat bran), *Artemisia carvifolia*, *Polygonum flaccidum Meissn.*, *Xanthium sibiricum* Patr., *Semen Armeniacae Amarum.*, and *Vigna umbellata*.

2 Claims, 2 Drawing Sheets
Specification includes a Sequence Listing.

Figure 2

SEQUENCE LISTING

<160> NUMBER OF SEQ ID NOS: 1

<210> SEQ ID NO 1
<211> LENGTH: 534
<212> TYPE: DNA
<213> ORGANISM: Penicillium chrysogenum

<400> SEQUENCE: 1

```
aggtcacctg gataaaaatt tgggttgatc ggcaagcgcc ggccgggcct acagagcggg    60
tgacaaagcc cctatcgctc gaggaccgga cgcggtgccg ccgctgcctt tcgggcccgt   120
cccccgggat cggagcacgg ggcccaacac acaagccgtg cttgagggca gaaatgacgc   180
tcgaacaggc atgcccccg gaataccagg gggcgcaatg tgcgttcaaa gactcgatga    240
ttcactgaat ttgcaattca cattacgtat cgcatttcgc tgcgttcttc atcgatgccg   300
gaaccaagag atccgttgtt gaaagttta aataatttat attttcactc agactacaat    360
cttcagacag agttcgaggg tgtcttcgga gggcgcggcg ccggggggcgt aagcccccg    420 gcggcacgtt aaggcgggcc cgccgaagca acaaggtaaa ataaacacgg gtgggaggtt   480
ggaccgagag ggccctcact cggtaatgat ccttccgcag gttcacctac ggaa          534
```

METHOD FOR THE PREPARATION OF MEDICATED LEAVEN MASSA BY PURE STRAIN FERMENTATION

CROSS REFERENCE OF RELATED APPLICATIONS

The present application claims the priority of Chinese Patent Application No. 201510340237.9, as filed on Jun. 19, 2015 and titled with "A method for the preparation of Medicated Leaven Massa by pure strain fermentation", and the disclosure of which is incorporated herein by reference.

FIELD

The present invention involves in the fields of bioengineering and Chinese medicine material production, especially involves in a method for the preparation of Medicated Leaven Massa, a Chinese medicine by pure strain fermentation using a single strain: *Penicillium chrysogenum*.

BACKGROUND

Medicated Leaven Massa, also known as Shenqu or Liuqu in Chinese, is one of the common digestion-promoting drugs; it is prepared by fermenting the juices of *Artemisia annua* Linn., *Polygonum* hydropiper L., and *Xanthium sibiricum* Patr. with powders of *Armeniacae semen amarum*. and *Vigna umbellata*, wheat bran and flour mixed in a certain proportion under suitable conditions. Medicated Leaven Massa is the most widely applied among the traditional fermented medicines. Medicated Leaven Massa is sweet and pungent in flavor, warm in nature, and belongs to the spleen and stomach meridian; it has the effect of promoting digestion, invigorating stomach, regulating stomach and spleen and anti-diarrhea.

The traditional preparation technology of Medicated Leaven Massa was fermentation using natural microbial strains in a particular season under natural conditions. Medicated Leaven Massa products of different origins or of the same origin but of different batches vary greatly due to various fermented circumstances and seasons all over the country, and even the unwanted strains were involved in the fermenting process, such as aflatoxin. As a result, the safety of Medicated Leaven Massa is seriously affected. Therefore, it is of great significance to standardize the fermented method of Medicated Leaven Massa.

In our previous study, the fermenting strain was first separated from the traditional fermented Medicated Leaven Massa and identified as *Penicillium chrysogenum*. The *Penicillium chrysogenum* has been used to produce the Medicated Leaven Massa with pure strain fermentation. This process reduces the contamination of unwanted strains, allows a controllable process technology and quality, and simplifies the process technology to ensure the effect of Medicated Leaven Massa. The method provides scientific evidence for standardizing the fermentation technology of Medicated Leaven Massa, and improves economic efficiency in production.

SUMMARY

The first object of the present invention is to provide a strain for the pure strain fermentation of Medicated Leaven Massa, which is *Penicillium chrysogenum*.

The second object of the present invention is to provide a method for preparing the Medicated Leaven Massa using pure strain fermentation.

The third object of the present invention is to provide a method for preparing the Medicated Leaven Massa with *Penicillium chrysogenum* as the fermentative strain.

The above objects of the present invention are achieved by the following technical solutions:

The *Penicillium chrysogenum* strain suitable for the preparation of Medicated Leaven Massa by pure strain fermentation is derived from the following process:

3 strains of fungi were separated from the traditionally fermented Medicated Leaven Massa by using streak plate method and hyphal tip purification method. The 3 strains of fungi were subject to micro-morphological identification by using biological microscope and molecular biological identification by using DNA sequencing to determine as *Aspergillus oryzae, Penicillium chrysogenum*, and *Cladosporium cladosporioides*, respectively. Identification of the fungi Identification of Funguses Genomic DNA of fungus separated from Medicated Leaven Massa was subject to sequence amplification using ITS4 and ITS5.

50 μL of the reaction system is as follows:

| Reaction components | Volume (μL) |
|---|---|
| Taq DNA polymerase (0.5 U/μL) | 0.35 |
| 10 × PCR buffer | 7 |
| Primer ITS4 (10 μM) | 2 |
| Primer ITS5 (10 μM) | 2 |
| dNTP (2.5 mM) | 4 |
| Template DNA | 1 |
| Sterilized deionized water | 33.65 |

Settings of Cycle Parameters:

Predenaturation at 95° C. for 5 min, denaturation at 95° C. for 30 s, annealing at 55° C. for 30 s, extension at 72° C. for 1 min, 30 cycles, and finally extension at 72° C. for 10 min.

After the reaction was completed, 5 μL of the amplified product was taken and subject to 1.0% agarose gel electrophoresis with an electric field intensity of 5 V/cm for 1 h, and detected whether the target bands are in line with expectations under a UV lamp.

The PCR-amplified target gene fragments were sequenced, the detected sequences were committed to NCBI and subjected to Blast alignment with known gene sequences in Gene Bank database to select the sequences with a similarity above 99% and a specific species status, Clustal X1.83 was applied for multiple sequence alignments, and meanwhile phylogenetic trees were constructed using software MEGA 5.0. The sequences for identifying these strains were FJ176474.1, JF440603.1, AM948960.1 and JF834167.1, and the homology with JF834167.1 was the highest (Max ident of Blast of 100%).

In addition, microbiological identification was entrusted to Institute of Microbiology, the Chinese Academy of Sciences for further detection and identification, and a detection report with a number of (2013) Microbiology Detection No. 240 was provided, wherein the identified conclusion was that under our laboratory conditions, according to a comprehensive analysis of the experimental data including culture characteristics, microscopic characteristics and rRNA gene sequences of the submitted results and the like, the identification result of the submitted strain (Strain No. SQ2) was *Penicillium chrysogenum*.

2. The original natural fermentation of Medicated Leaven Massa was replaced by single strain fermentation, the odor and appearance after fermentation were observed, wherein the Medicated Leaven Massa fermented with *Penicillium chrysogenum* has a pure and fragrant odor, and a yellow skin appears on the surface which is consistent with the traditional fermentation; the Medicated Leaven Massa fermented with *Cladosporium* cladosporioides produced a rotten odor, and the fermentative blocks had a dark taupe surface which differed greatly from that of traditional fermentation, and it is speculated that *Cladosporium* cladosporioides is an unwanted strain, while *Penicillium chrysogenum* is an effective strain suitable for the pure strain fermentation of Medicated Leaven Massa.

3. The inhibition on 8 enteropathogenic bacteria by 95% ethanol extract of Medicated Leaven Massa fermented with *Penicillium chrysogenum* was examined. The results showed that the extract of the Medicated Leaven Massa fermented with *Penicillium chrysogenum* inhibited the growth of enteropathogenic bacteria significantly. The content of aflatoxin B1 in the Medicated Leaven Massa fermented with *Aspergillus oryzae* and *Penicillium chrysogenum* were detected by an ELISA kit, and it is acquired that the content of aflatoxin B1 in the Medicated Leaven Massa fermented with *Aspergillus oryzae* was 14.25 µg/kg, which is above the standard; the content of aflatoxin B1 in the Medicated Leaven Massa fermented with *Penicillium chrysogenum* is 1.63 µg/kg, which meets the requirement of content limitation.

A method for the preparation of Medicated Leaven Massa by pure strain fermentation, characterized in that the Medicated Leaven Massa is prepared by fermentation under suitable conditions with a single fermentative strain and a culture medium made of 6 ingredients including flour (and/or wheat bran), *Artemisia annua* Linn., *Polygonum hydropiper* L., *Xanthium sibiricum* Patr., *Armeniacae semen amarum*, and *Vigna umbellata*.

A microbial strain for the preparation of Medicated Leaven Massa by pure strain fermentation, characterized in that the strain is *Penicillium chrysogenum*.

A method for the preparation of Medicated Leaven Massa by pure strain fermentation with *Penicillium chrysogenum* as the fermentative strain.

A method for the preparation of Medicated Leaven Massa by pure strain fermentation with *Penicillium chrysogenum*, characterized in the following steps:

A certain amount of *Artemisia annua* Linn., *Polygonum hydropiper* L., and *Xanthium sibiricum* Patr. were weighed and made into juice to be used as an adhesive for preparing fermentative soft material; wheat bran and flour with a ratio of the two of 1:5~5:1 are weighed, into which *Armeniacae semen amarum* powder in a proportion of 3-7% with respect to the mixture weight of the wheat bran and the flour, and then *Vigna umbellata* powder in a proportion of 3-7% with respect to the mixture weight of the wheat bran and the flour are added, and the above materials are well mixed and constitute together a solid culture medium needed for the fermentation, providing carbon source and nitrogen source needed for the fermentation; the *Penicillium chrysogenum* strain is mixed into the solid culture medium in a proportion of 1-5 g of the strain added per 100 g of the mixed solid culture medium; they are well mixed, made into soft material, then made into fermentative blocks, placed under a constant temperature condition of 28~32° C. with a humidity of 70-80%, cultured for 5-10 d until a yellow skin has been all over the surface, stopped from fermenting, taken out, cut into fermentative blocks sized about 1 cm³, and dried to obtain the Medicated Leaven Massa by pure strain fermentation.

There are clear differences between the method for the preparation of Medicated Leaven Massa in the present invention and that of the currently commercially available Medicated Leaven Massa. The inventive method uses a direct fermentation method, after making *Artemisia annua* Linn., *Polygonum hydropiper* L., and *Xanthium sibiricum* Patr. into juice places it in the culture medium made by mixing flour and/or wheat bran, *Armeniacae semen amarum* and *Vigna umbellata* after inoculating the *Penicillium chrysogenum* separated by biological techniques carries out fermentation, specifies precise fermentation time and temperature, reduces the contamination of unwanted strains, and simplifies the operation. The Medicated Leaven Massa prepared by this method maintains the characteristics of the traditional Medicated Leaven Massa and overcomes the deficiencies of the traditional fermentation, the fermented product of the novel method may produce a better pharmaceutical effect, has significant inhibitory and bactericidal activity against common pathogens of human body, and produces a digestion-promoting effect, and this method is suitable for industrial mass production.

DESCRIPTION OF THE DRAWINGS

Figure 2:
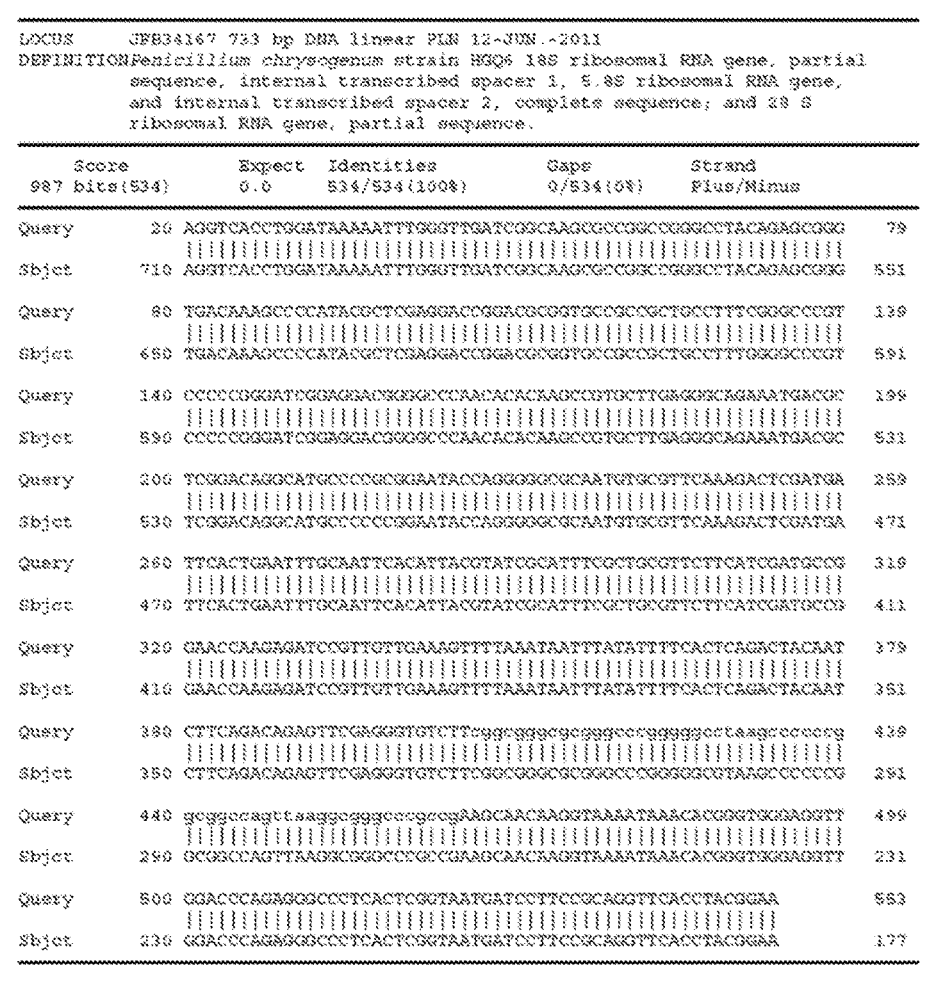

FIG. 2 is Blast result of *Penicillium chrysogenum* sequence of the present invention and JF834167.1 of Gene Bank database.

DETAILED DESCRIPTION

Figure 1:
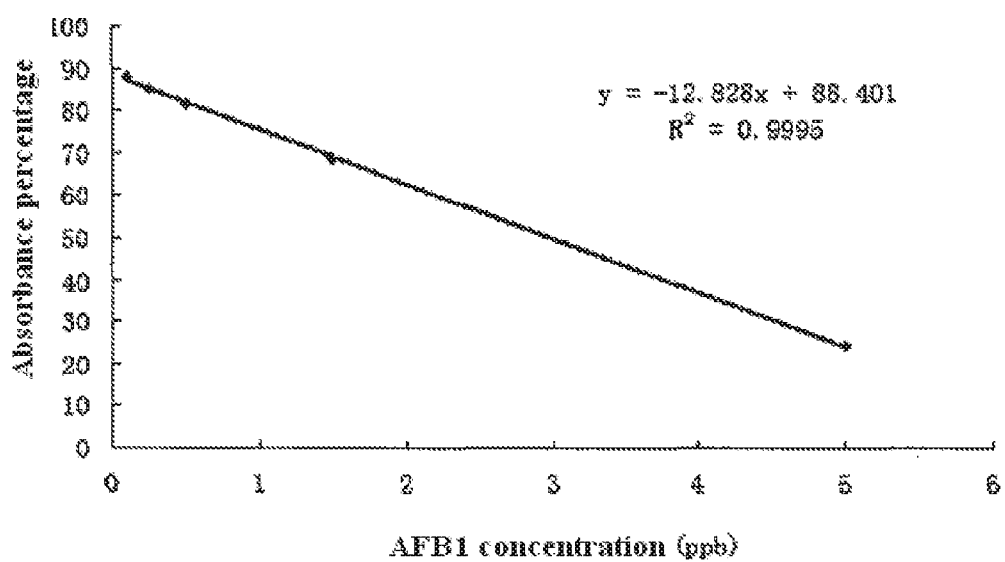
FIG. 1 is the standard curve of aflatoxin B1.

The present invention is further described below in conjunction with specific examples, and advantages and features of the present invention will become clearer with the description. However, these examples are only exemplary, without constituting any limitation to the scope of the present invention.

It is to be understood by those skilled in the art that modifications or replacements may be made to the details and forms of the present technical solutions without departing from the spirit and scope of the present invention, but these modifications and replacements all fall into the protection scope of the present invention.

Example 1: Preparation of Medicated Leaven Massa by Laboratory Fermentation of *Penicillium chrysogenum*

25 g of dried *Artemisia annua* Linn., *Polygonum hydropiper* L., and *Xanthium sibiricum* Patr. each were weighed, distilled water 10, 8 and 6 times the amount was added and decocted 3 times for 40 min each time, and the water decoctions were combined, concentrated to 250 mL, transferred to a 500 mL sterilized conical flask, sealed, placed on a clean workbench and left to cool for use.

500 g of wheat bran, 500 g of flour and 40 g of *Armeniacae semen amarum* and *Vigna umbellata* powder each were weighed, held in a 1000 mL beaker which was sealed by 8 layers of gauze placed between kraft papers, sterilized under 103.4 kPa at 121.3° C. in a steam autoclave for 20 min, taken out immediately after the sterilization was completed, transferred to a clean workbench and left to cool for use.

The medicine juice processed above and 20 g of *Penicillium chrysogenum* were mixed into the sterile culture medium, well admixed, made into a round-cake shape having a diameter of about 12 cm and a thickness of about 1 cm, held in a sterilized dish having a caliber of 18 cm, placed upside-down in an incubator at 28° C. with a relative humidity of 70%, cultured for 7 d until a yellow skin appeared, stopped from fermenting, taken out, cut into fermentative blocks sized about 1 cm$^3$, dried and collected for storage, and mothproofing was to be noticed.

Example 2: Preparation of Medicated Leaven Massa with *Penicillium Chrysogenum* in Production 5 kg of fresh *Artemisia annua* Linn., *Polygonum hydropiper* L., and *Xanthium sibiricum* Patr. each were weighed and squeezed for fresh juice as an adhesive for use.

30 kg of wheat bran, 20 kg of flour and 2 kg of *Armeniacae semen amarum* and *Vigna umbellata* powder each were weighed, the fresh juice processed above and 100 g of *Penicillium chrysogenum* were mixed into the sterile culture medium, well admixed, made into 20×12×8 cm fermentative blocks, stacked in an inverted "T" shape, covered by wet substances, cultured for 10 d at 30° C. with a relative humidity of 75% until a yellow skin appeared, stopped from fermenting, taken out, cut into fermentative blocks sized about 1 cm$^3$ and dried to obtain it, and this method is suitable for production use.

Experimental Example 1: Examination of Minimal Inhibitory Concentration

Medicated Leaven Massa produces the pharmaceutical effect of inhibiting enteric flora disturbance by an inhibitory mechanism, and thus the present experiments examined the raw materials for Medicated Leaven Massa fermentation, commercially available Medicated Leaven Massa and the Medicated Leaven Massa from pure strain fermentation with *Penicillium chrysogenum* for their inhibitory activities:

Sample A: 10 g of dried *Artemisia annua*, Siberian Cocklebur and *Polygonum* hydropiper and 2 g of the powders of *Armeniacae semen amarum* and *Vigna umbellata* each were taken, distilled water 10, 8 and 6 times (v/m) the amount were added to extract 3 times respectively, for 1 h each time, and the extracts were combined, concentrated and then dried under reduced pressure for 72 h to obtain the extract of Sample A, i.e. the extract of raw materials for Medicated Leaven Massa without the addition of flour and wheat bran.

Sample B: 100 g of commercially available Medicated Leaven Massa was taken, 95% ethanol 10, 8 and 6 times (v/m) were added to extract 3 times respectively, for 1 h each time, and the extracts were combined and subjected to rotary evaporation to recover the solvent, and then dried under reduced pressure for 72 h to obtain the extract of Sample B.

Sample C was the Medicated Leaven Massa samples fermented with a single strain of *Penicillium chrysogenum* and fried respectively, 100 g of each sample was weighted and the extracted method was the same as that of Sample B.

1.0024 g of Sample A, 0.3750 g of Sample B and 0.3015 g of Sample C were weighted precisely and placed in 5 mL volumetric flasks respectively, 200 mL DMSO was added to promote the dissolution, and finally distilled water was added to volume to formulate test samples having concentrations of 200.5 mg/mL, 75.0 mg/mL and 60.3 mg/mL respectively; in addition, a 4% DMSO aqueous solution was formulated as a blank control.

The minimal inhibitory concentration (MIC) was determined by serial dilution method on 96-well plate. The following solutions were added to a clean sterile 96-well plate: 100 µL of nutrient broth culture medium was added to the 96-well plate; 100 µL of the sample was added to the 1st well and The well was mixed with the culture medium, then 100 µL of it was taken out and added to the 2nd well and so forth to the 10th well, and 100 µL of it was taken out and disposed in a waste liquid of 75% ethanol; 100 µL of nutrient broth culture medium was further added to the 11th well; 100 µL of bacteria solution for experimental use was added to each well except the 12th well and well mixed, and the above processes were sterile operation.

At this point, the n well corresponded to a medicine concentration of $C_0/2^{n+1}$ ($C_0$ was the initial concentration), wherein the 11th well was a medicine blank and the 12th well was a bacteria blank, and each sample was tested 3 times at the same time. The results were observed after being cultured at a constant temperature of 37° C. for 18 h.

The minimal bactericidal concentration (MBC) was determined by an agar-plate zoning method, each of the above bacteria/medicine mixed solutions without bacterial growth was inoculated on nutrient agar culture medium and cultured at a constant temperature of 37° C. for 24 h, and the bacterial growth was observed.

Examination Results of the Inhibitory Effect

Except that the DMSO blank group had no inhibitory effect, all the other three samples had an inhibitory effect at different degrees, wherein Sample A, the extract of raw materials for Medicated Leaven Massa except culture medium, had a relatively weaker inhibitory effect. After being subject to pure strain fermentation with a single strain, Sample C had a significantly inhibitory effect which higher than that of Sample B and commercially available Medicated Leaven Massa. The experiments showed that the raw materials for Medicated Leaven Massa had a significant inhibitory effect superior to that of the commercially available product after being fermented with *Penicillium chrysogenum* (Table 1-4).

TABLE 1

Minimal inhibitory concentration (MIC) of Sample A

| Sample A | Inhibition in the sample well with the corresponding concentration (mg/mL) | | | | | Medicine blank | Bacteria blank | Minimal inhibitory concentration MIC (mg/mL) |
|---|---|---|---|---|---|---|---|---|
| | 50.12 | 25.06 | 12.53 | 6.26 | 3.13 | | | |
| *Shigella dysenteriae* | − | − | + | + | + | − | + | 25.06 |
| *Escherichia coli* | − | − | + | + | + | − | + | 25.06 |
| *Staphylococcus albus* | − | − | + | + | + | − | + | 25.06 |
| *Staphylococcus citreus* | − | − | + | + | + | − | + | 25.06 |

TABLE 1-continued

Minimal inhibitory concentration (MIC) of Sample A

| Sample A | \multicolumn{5}{c}{Inhibition in the sample well with the corresponding concentration (mg/mL)} | | | Minimal inhibitory concentration |
|---|---|---|---|---|---|---|---|---|
| | 50.12 | 25.06 | 12.53 | 6.26 | 3.13 | Medicine blank | Bacteria blank | MIC (mg/mL) |
| Shigella flexneri | − | − | + | + | + | − | + | 25.06 |
| Staphylococcus aureus | − | − | + | + | + | − | + | 25.06 |
| Salmonella paratyphi B | − | − | + | + | + | − | + | 25.06 |
| β-Streptococcus haemolyticus | − | − | + | + | + | − | + | 25.06 |

Note:
Sample A was the extract of raw materials for Medicated Leaven Massa, "−" indicates no bacterial growth in this well, and "+" indicates bacterial growth in this well.

TABLE 2

Minimal inhibitory concentration (MIC) of Sample B

| Sample B | \multicolumn{5}{c}{Inhibition in the sample well with the corresponding concentration (mg/mL)} | | | Minimal inhibitory concentration |
|---|---|---|---|---|---|---|---|---|
| | 18.75 | 9.38 | 4.69 | 2.35 | 1.18 | Medicine blank | Bacteria blank | MIC (mg/mL) |
| Shigella dysenteriae | − | − | − | + | + | − | + | 4.69 |
| Escherichia coli | − | − | − | + | + | − | + | 4.69 |
| Staphylococcus albus | − | − | − | + | + | − | + | 4.69 |
| Staphylococcus citreus | − | − | − | + | + | − | + | 4.69 |
| Shigella flexneri | − | − | − | + | + | − | + | 4.69 |
| Staphylococcus aureus | − | − | − | + | + | − | + | 4.69 |
| Salmonella paratyphi B | − | − | − | + | + | − | + | 4.69 |
| β-Streptococcus haemolyticus | − | − | − | + | + | − | + | 4.69 |

Note:
Sample B was the extract of commercially available Medicated Leaven Massa, "−" indicates no bacterial growth in this well, and "+" indicates bacterial growth in this well.

TABLE 3

Minimal inhibitory concentration (MIC) of Sample C

| Sample C | \multicolumn{5}{c}{Inhibition in the sample well with the corresponding concentration (mg/mL)} | | | Minimal inhibitory concentration |
|---|---|---|---|---|---|---|---|---|
| | 15.08 | 7.54 | 3.77 | 1.84 | 0.94 | Medicine blank | Bacteria blank | MIC (mg/mL) |
| Shigella dysenteriae | − | − | − | − | + | − | + | 1.84 |
| Escherichia coli | − | − | − | − | + | − | + | 1.84 |
| Staphylococcus albus | − | − | − | − | + | − | + | 1.84 |
| Staphylococcus citreus | − | − | − | + | + | − | + | 3.77 |
| Shigella flexneri | − | − | − | − | + | − | + | 1.84 |
| Staphylococcus aureus | − | − | − | − | + | − | + | 1.84 |
| Salmonella paratyphi B | − | − | − | − | + | − | + | 1.84 |
| β-Streptococcus haemolyticus | − | − | − | − | + | − | + | 1.84 |

Note:
Sample C was the extract of the Medicated Leaven Massa fermented with a single strain of *Penicillium chrysogenum*, "−" indicates no bacterial growth in this well, and "+" indicates bacterial growth in this well.

TABLE 4

Minimal bactericidal concentration (MBC)

| Strain | Sample A | Sample B | Sample C |
|---|---|---|---|
| Shigella dysenteriae | — | 4.69 | 1.84 |
| Escherichia coli | — | 9.38 | 1.84 |
| Staphylococcus albus | — | 4.69 | 1.84 |
| Staphylococcus citreus | — | 4.69 | 3.77 |
| Shigella flexneri | — | 9.38 | 1.84 |
| Staphylococcus aureus | — | 4.69 | 1.84 |
| Salmonella paratyphi B | — | 4.69 | 1.84 |
| β-Streptococcus haemolyticus | — | 4.69 | 1.84 |

Note:
"—" indicates no Minimal bactericidal concentration, Sample A was the extract of raw materials for Medicated Leaven Massa, Sample B was the extract of commercially available Medicated Leaven Massa, and Sample C was the extract of the Medicated Leaven Massa fermented with a single strain of Penicillium chrysogenum, Experimental Example 2: Determination of the Content of Aflatoxin B1

Pretreatment of the samples: the samples of the Medicated Leaven Massa fermented with a single strain of Aspergillus oryzae and Penicillium chrysogenum were pulverized and sieved with a 50-mesh sieve, respectively. 5 g of the two samples were weighted, 25 mL of sample extract was added, shaken for 10 min, and centrifuged at 4000 r/min for 5 min, 5 mL of the supernatant was taken, 10 mL of dichloromethane was added, shaken for 5 min, centrifuged and stratified, the lower layer of the dichloromethane phase was taken for use, 10 mL of dichloromethane was further added to the upper layer of the water phase, the extraction was repeated once, and the dichloromethane phases were combined. It was blow-dried with nitrogen at 50° C., 2 mL of sample extract was added to dissolve the volatiles, and 8 mL of sample diluent was further added for dilution to obtain the sample solution to be tested.

Determination of absorbance: The required reagents were taken out from a refrigerated environment before the experiments, and balanced to room temperature (20~25° C.). A required number of microplates were taken out, 50 μL of the standard or the sample was added to the corresponding micro well, ABF1 enzyme label was added at 50 μL/well, shaken gently and well mixed. After being covered by a covering film, the plate was placed in a dark environment at 25° C. for reaction for 30 min, the covering film was carefully lifted, the liquid within the wells was spin-dried, and it was washed adequately 5 times at an interval between each time of 30 s with a washing solution at 300 μL/well, and patted to dry with absorbent paper. Substrate A solution at 50 μL/well and then substrate B solution at 50 μL/well were added, shaken gently and well mixed, and after being covered by a covering film, the plate was placed in a dark environment at 25° C. for reaction for 15 min. A stopping solution 50 μL/well was added and shaken gently for well mixed, and the microplate reader was set at 450 nm to determine the OD value of each well.

Determination Results of the Content of Aflatoxin B1

(1) Determination of the Absorbance Percentage of the Standard

The absorbance percentage of the standard equals the mean absorbance of the standard divided by the absorbance of the first standard (i.e. 0 standard) and then multiplied by 100%, that is, absorbance percentage (%)=$B/B_0 \times 100\%$.

B stands for the mean absorbance of the standard solution.

$B_0$ stands for the mean absorbance of the 0 (ppb) sample solution.

The measured absorbance percentages of the standard are seen in Table 5.

TABLE 5

Absorbance percentages of the standard

| No. | Standard concentration (ppb) | Mean absorbance B | Absorbance percentage $B/B_0$ (%) |
|---|---|---|---|
| $B_0$ | 0 | 1.928 | |
| $B_1$ | 0.1 | 1.696 | 87.97 |
| $B_2$ | 0.25 | 1.640 | 85.06 |
| $B_3$ | 0.5 | 1.576 | 81.74 |
| $B_4$ | 1.5 | 1.320 | 68.46 |
| $B_5$ | 5 | 0.472 | 24.48 |

Note:
B0-B5 is the standards given in a test kit.

(2) Plotting of the Standard Curve

The standard curve was plotted with the absorbance percentage of the standard as the vertical ordinate and the concentrations of the aflatoxin B1 standard (ppb) as the horizontal ordinate (see FIG. 1).

(3) Determination of the Absorbance Percentage of the Sample

The absorbance percentage of the sample equals the mean absorbance of the samples divided by the absorbance of the first standard (i.e. 0 standard) and then multiplied by 100%, that is, absorbance percentage (%)=$\overline{A}/B_0 \times 100\%$.

$\overline{A}$ stands for mean absorbance of the sample solutions $B_0$ stands for mean absorbance of the 0 (ppb) sample solution The calculation method of the absorbance percentage of the sample was the same as above, and the results are seen in Table 6.

TABLE 6

Absorbance of the sample and content of aflatoxin B1

| | Absorbance A | Absorbance percentage $\overline{A}/B_0$ (%) | Residue of aflatoxin B1 (μg/kg) |
|---|---|---|---|
| Fermented product with Aspergillus oryzae | 1.352 | 70.12 | 14.25 |
| Fermented product with Penicillium chrysogenum | 1.664 | 86.31 | 1.63 |

As can be seen from the experimental results, the residue of aflatoxin B1 in the Medicated Leaven Massa fermented with Aspergillus oryzae was 14.25 μg/kg, which was higher than the Chinese Pharmacopoeia standard 5 μg/kg, the residue of aflatoxin B1 in the Medicated Leaven Massa fermented with Penicillium chrysogenum was 1.63 μg/kg, which was lower than Chinese Pharmacopoeia standard 5 μg/kg. Thereby it can be speculated that Aspergillus oryzae as an unwanted strain for Medicated Leaven Massa fermentation is the main source of aflatoxin.

What is claimed is:

1. A method for preparing Medicated Leaven Massa, comprising:
    using *Penicillium chrysogenum* as a single strain for fermentation, wherein a culture medium for the fermentation is made from flour or a combination of flour and wheat bran, and *Armeniacae semen amarum*, *Vigna umbellata*, *Artemisia annua* Linn., *Polygonum hydropiper* L. and *Xanthium sibiricum* Patr., and performing the fermentation at a temperature of 28~32° C., humidity of 70~80%, and a culture time of 5~10 days.

2. The method for preparing Medicated Leaven Massa according to claim 1, further comprising:
    weighing *Armeniacae semen amarum*, *Polygonum hydropiper* L. and *Xanthium sibiricum* Patr. and extracting juice therefrom to prepare an adhesive for the fermentation;
    weighing wheat bran and flour with a ratio of 1:5~5:1,
    adding *Armeniacae semen amarum* powder and *Vigna umbellata* powder in a proportion of 3~7% of the weight of total wheat bran and flour,
    mixing the above materials together to form a solid culture medium for the fermentation;
    adding *Penicillium chrysogenum* into the solid culture medium in a proportion of 1~5 g of *Penicillium chrysogenum* per 100 g of the solid culture medium, and mixing well to make a soft material;
    forming the soft material into fermentative blocks;
    using the blocks for fermentation until a yellow skin is all over the surface of the blocks; and
    cutting the blocks into pieces of about 1 cm$^3$, and drying to obtain the Medicated Leaven Massa.

\* \* \* \* \*